(12) United States Patent
Wallace et al.

(10) Patent No.: US 7,608,089 B2
(45) Date of Patent: Oct. 27, 2009

(54) VASO-OCCLUSIVE DEVICE HAVING PIVOTABLE COUPLING

(75) Inventors: Michael P. Wallace, Fremont, CA (US); Kamal Ramzipoor, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 376 days.

(21) Appl. No.: 11/022,189

(22) Filed: Dec. 22, 2004

(65) Prior Publication Data

US 2006/0135986 A1    Jun. 22, 2006

(51) Int. Cl.
A61M 29/00    (2006.01)
(52) U.S. Cl. ..................................... 606/200
(58) Field of Classification Search .............. 606/200, 606/108
See application file for complete search history.

(56) References Cited

U.S. PATENT DOCUMENTS

| | | |
|---|---|---|
| 4,994,069 A | 2/1991 | Richart et al. |
| 5,122,136 A | 6/1992 | Guglielmi et al. |
| 5,226,911 A | 7/1993 | Chee et al. |
| 5,234,437 A | 8/1993 | Sepetka |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,350,397 A | 9/1994 | Palermo et al. |
| 5,354,295 A | 10/1994 | Guglielmi et al. |
| 5,382,259 A | 1/1995 | Phelps et al. |
| 5,549,624 A | 8/1996 | Mirigian et al. |
| 5,690,666 A | 11/1997 | Berenstein et al. |
| 5,853,418 A | 12/1998 | Ken et al. |
| 5,941,888 A | 8/1999 | Wallace et al. |

(Continued)

OTHER PUBLICATIONS

PCT International Search Report for PCT/US2005/046289, Applicant: Boston Scientific Scimed, Inc., Forms PCT/ISA/210 and 220, dated May 19, 2005 (6 pages).

(Continued)

*Primary Examiner*—(Jackie) Tan-Uyen T Ho
*Assistant Examiner*—Melanie Tyson
(74) *Attorney, Agent, or Firm*—Vista IP Law Group LLP

(57) ABSTRACT

An assembly for occluding a vascular site (e.g., an aneurysm) of a human or veterinary patient includes a vaso-occlusive member, a pusher member having a distal end and a severable junction located proximal to the distal end, and a pivotable coupling that couples the pusher member to the occlusive member. A delivery catheter can be used to deliver the vaso-occlusive member to the vascular site. A method of using the assembly to occlude an aneurysm having an aneurysmal sac and an aneurysmal neck, includes locating the catheter within the aneurysmal neck, and manipulating the pusher member to place the vaso-occlusive member within the aneurysmal sac. The method further includes severing the severable junction to detach the vaso-occlusive member from the pusher member. As a result, an axial force is applied by the vaso-occlusive member in a proximal direction, which buckles the pivotable coupling to laterally deflect the axial force. The lateral deflection of the axial force caused by the buckling of the pivotable coupling prevents the catheter from being displaced from the aneurysmal neck by the axial force.

5 Claims, 6 Drawing Sheets

U.S. PATENT DOCUMENTS

| | | | |
|---|---|---|---|
| 5,944,733 A | 8/1999 | Engelson et al. | |
| 6,165,178 A * | 12/2000 | Bashiri et al. | 606/108 |
| 6,193,728 B1 | 2/2001 | Ken et al. | |
| 6,280,457 B1 | 8/2001 | Wallace et al. | |
| 6,500,149 B2 | 12/2002 | Gandhi et al. | |
| 6,905,503 B2 * | 6/2005 | Gifford et al. | 606/108 |
| 2003/0130689 A1 | 7/2003 | Wallace et al. | |
| 2004/0002731 A1 * | 1/2004 | Aganon et al. | 606/200 |
| 2004/0034378 A1 * | 2/2004 | Monstadt et al. | 606/157 |
| 2004/0199175 A1 | 10/2004 | Jaeger et al. | |
| 2004/0204701 A1 * | 10/2004 | Cox et al. | 606/1 |

OTHER PUBLICATIONS

PCT Written Opinion of the International Search Authority for PCT/US2005/046289, Applicant Boston Scientific Scimed, Inc., Form PCT/ISA/237, dated May 19, 2005 (4 pages).

* cited by examiner

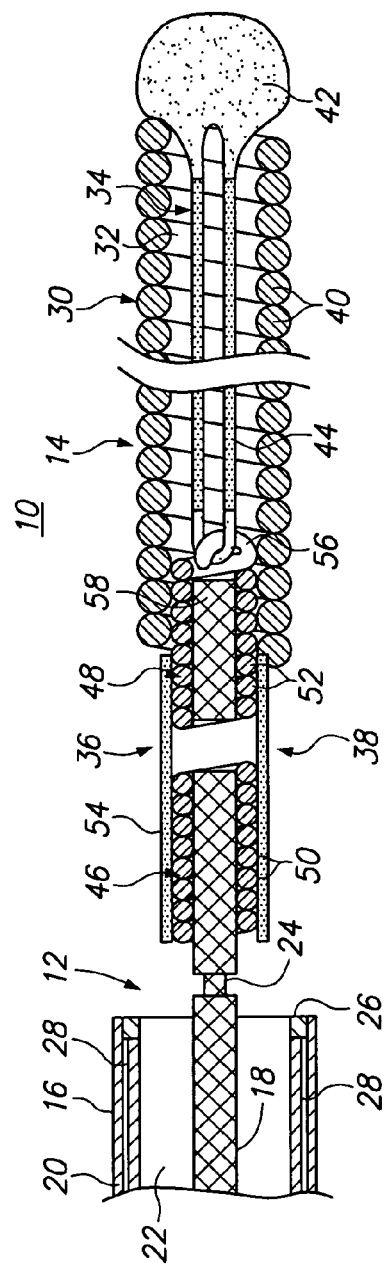
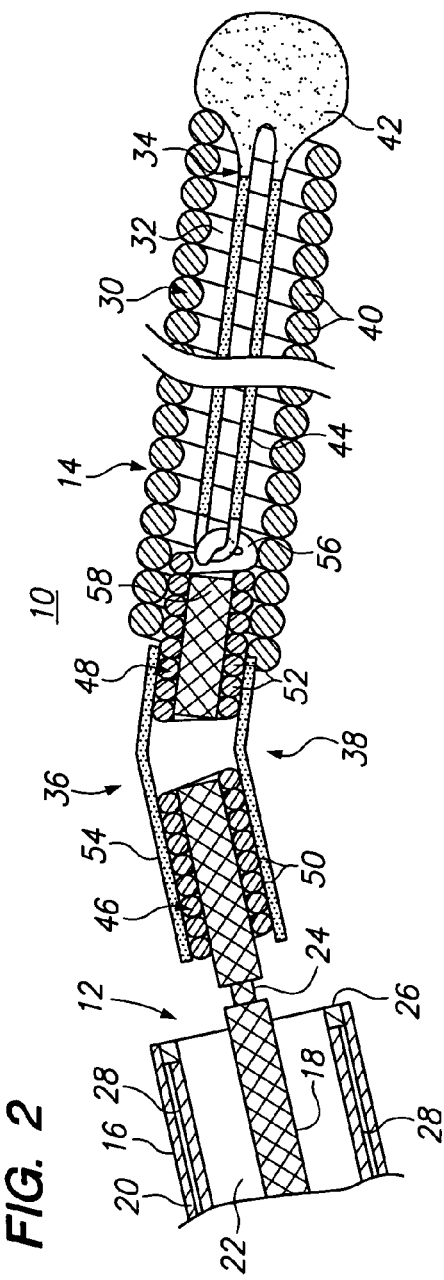
FIG. 1
FIG. 2

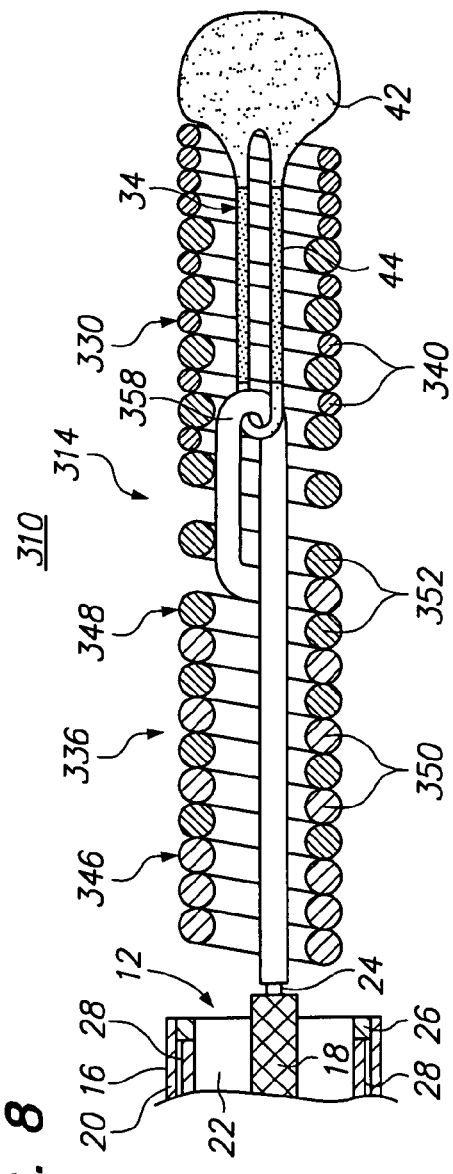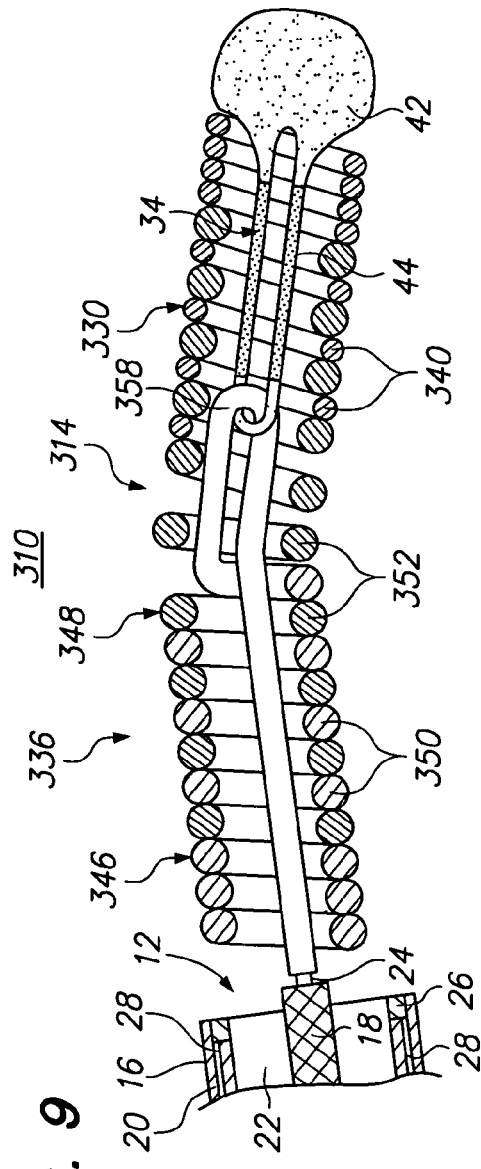

VASO-OCCLUSIVE DEVICE HAVING PIVOTABLE COUPLING

FIELD OF THE INVENTION

The present invention relates to assemblies for implanting vaso-occlusive devices in-vivo for establishing an embolus or vascular occlusion in a vessel of a human or veterinary patient.

BACKGROUND OF THE INVENTION

Vaso-occlusive devices or implants are used for a wide variety of reasons. They are often used for treatment of intravascular aneurysms. This is to say that the treatment involves the placement of a vaso-occlusive device in an aneurysm to cause the formation of a clot and eventually of a collagenous mass containing the vaso-occlusive device. These occlusions seal and fill the aneurysm thereby preventing the weakened wall of the aneurysm from being exposed to the pulsing blood pressure of the open vascular lumen. Treatment of aneurysms in this fashion is a significant improvement over the surgical method typically involved.

A common vaso-occlusive device is a soft, helically wound coil. A typical commercial coil will be formed by winding a platinum wire strand about a primary mandrel and applying a heat treatment to impart a primary winding coil shape. The relative stiffness of the coil will depend, among other things, on the diameter of the wire strand, the diameter of the primary mandrel, and the pitch of the primary windings. The device is then wrapped around a secondary mandrel, and again heat treated to impart a secondary shape. For example, U.S. Pat. No. 4,994,069, to Ritchart et al., describes a vaso-occlusive coil that assumes a primary, linear helical configuration when stretched and a folded, and a convoluted, secondary configuration when relaxed in a minimal energy configuration. The stretched condition is used in placing the coil at the desired site (by its passage through a delivery catheter) and the coil assumes a relaxed configuration—which is better suited to occlude the vessel—once the device is so placed.

It is well-known to detach such vaso-occlusive coil devices from a delivery wire using a mechanical detachment mechanism. For example, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter.

It is also well-known to use an electrolytically severable joint to release vaso-occlusive coils at the vessel site. For example, Guglielmi et al. shows an embolism forming device and procedure for using that device which employs an electrolytically severable joint. Specifically, Guglielmi et al. desirably places a finely wound platinum coil into a vascular cavity such as an aneurysm. The coil is delivered endovascularly using a catheter such as those described above. After placement in the aneurysm, the coil is severed from its insertion core wire by the application of a small electric current to that core wire. The deliverable coils are said to be made of a platinum material. Proximal of the embolic coil, as noted above, is a core wire which is typically stainless steel. The core wire is used to push the platinum embolic coil into vascular site to be occluded. Other variations of the Guglielmi et al. technology are found in U.S. Pat. No. 5,354,295.

Current electrolytically detachable coil products employ a relatively inflexible bridge assembly that connects the proximal end of the vaso-occlusive coil to the distal end of the pusher wire assembly. When the coil is detached from the pusher wire, the force the pusher wire has been exerting on the coil (and aneurysm wall) pushes back on the pusher wire assembly, which can displace the tip of the introducer catheter out of the aneurysm. This is because the PET sleeve does not laterally buckle or flex, but instead axially transmits the pushback force against the distal tip of the delivery catheter. Having the catheter tip displaced from the aneurysm requires the physician to relocate the catheter tip prior to placement of a further occlusive device, which undesirably extends the duration of the procedure.

SUMMARY OF THE INVENTION

In accordance with one aspect of the invention, an assembly is provided for establishing an embolus or vascular occlusion in a vessel of a human or veterinary patient. The assembly generally includes a vaso-occlusive member (e.g., a coil), a pusher member having a distal end and a severable junction (e.g., a mechanically or electrolytically severable junction) located proximal to the distal end, and a pivotable coupling that couples the pusher member to the occlusive device. The assembly may optionally comprise a catheter in which the pusher member is slidably disposed. If the vaso-occlusive member comprises a coil, the assembly may optionally comprise a stretch-resisting member, in which case, the pivotable coupling may anchor the stretch-resisting member within the lumen of the coil. Besides optionally providing anchoring for a stretch-resisting member, the pivotable coupling may also include an element that electrically insulates the pusher member distal end from vaso-occlusive member. The pivotable coupling may be fashioned in any one of a variety of manners.

In one embodiment, the pivotable coupling comprises a flexible sleeve (e.g., one made of an elastomeric material) coupled between the pusher member distal end and vaso-occlusive member. The pivotable coupling may also comprise a proximal coil coupled to the pusher member distal end, and a distal coil coupled to the vaso-occlusive member, in which case, the sleeve is disposed over the proximal and distal coils.

In another embodiment, the pivotable coupling comprises a proximal link member (e.g., a hook or loop) coupled to the pusher member distal end, and a distal link member (e.g., a hook or loop) coupled to the vaso-occlusive member, wherein the proximal and distal link members pivotably engage each other. The pivotable coupling may also comprise a proximal coil coupled to the pusher member distal end, and a distal coil coupled to the vaso-occlusive member, in which case, the proximal link member is disposed on a distal end of the proximal coil, and the distal link member is disposed on a proximal end of the distal coil.

In still another embodiment, the pivotable coupling comprises a first ball member coupled to the pusher member distal end, a second ball member coupled to the vaso-occlusive member, and a sleeve (e.g., a braid or mesh) holding the first and second ball members. The pivotable coupling may also comprise a coil mounted to the vaso-occlusive member, in which case, the first ball member is formed onto the pusher member distal end, and the second ball member is formed on a proximal end of the coil.

In yet another embodiment, the pivotable coupling comprises a first coil coupled between the pusher member distal end and the vaso-occlusive member. The first coil comprises open-pitched windings between which spaces reside. The vaso-occlusive member comprises a vaso-occlusive coil comprising proximal windings disposed within the spaces between some of the open-pitched windings. At least some of the spaces between the open-pitched windings remain empty. The pivotable coupling may comprises a second coil coupled between the pusher member distal end and the first coil, in which case, the second coil comprises distal windings disposed within the spaces between some of the open-pitched windings.

In accordance with another aspect of the invention, a method of occluding a vascular site (e.g., an aneurysm) using the vaso-occlusive assembly is provided. The method comprises manipulating the pusher member to place the vaso-occlusive member adjacent the vascular site. If the vascular site is an aneurysm, the delivery catheter can be placed within the aneurysmal neck, and the pusher member can be manipulated to place the vaso-occlusive member within the aneurysmal sac. The method further comprises severing the severable junction to detach the vaso-occlusive member from the pusher member. As a result, an axial force is applied by the vaso-occlusive member in a proximal direction, which buckles the pivotable coupling to laterally deflect the axial force. If the catheter is in an aneurysmal neck, the lateral deflection of the axial force caused by the buckling of the pivotable coupling will prevent the catheter from being displaced from the aneurysmal neck by the axial force.

Other features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1 is a cross-sectional view of a vaso-occlusive assembly constructed in accordance with a preferred embodiment of the present inventions;

FIG. 2 is a cross-sectional view of the vaso-occlusive assembly of FIG. 1, particularly illustrating operation of a pivotable coupling within the assembly;

FIG. 8 is a cross-sectional view of a vaso-occlusive assembly constructed in accordance with yet another preferred embodiment of the present inventions;

FIG. 9 is a cross-sectional view of the vaso-occlusive assembly of FIG. 8, particularly illustrating operation of a pivotable coupling within the assembly;

DETAILED DESCRIPTION OF THE PREFERRED EMBODIMENTS

Figure 3:
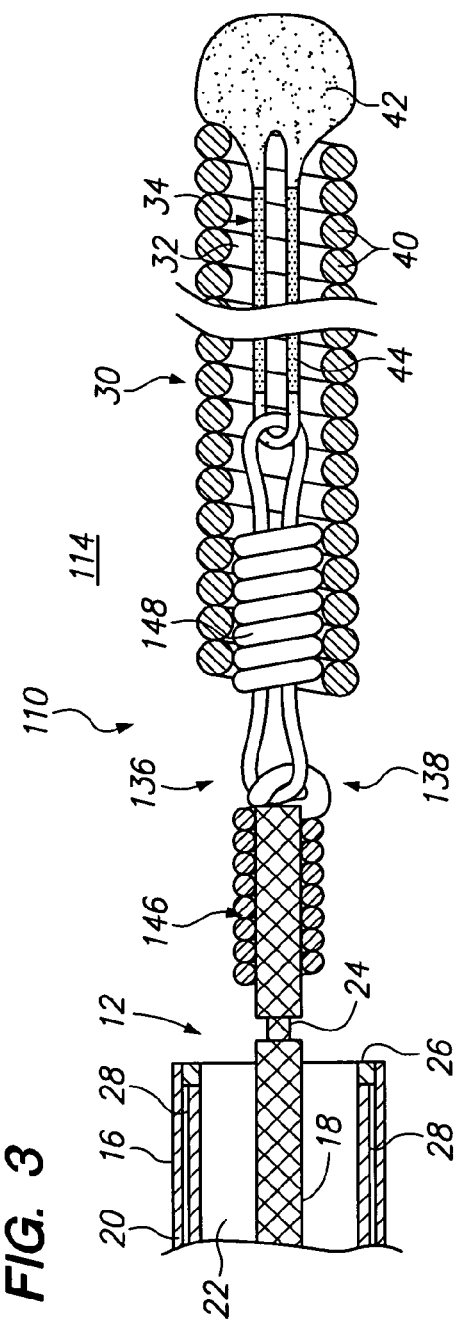
FIG. 3 is a cross-sectional view of a vaso-occlusive assembly constructed in accordance with another preferred embodiment of the present inventions.

Referring to FIG. 1, a vaso-occlusive assembly 10 constructed in accordance with a preferred embodiment is illustrated. For purposes of orientation, the term "proximal" as it qualifies an element generally refers to the left end of the element, and the term "right" as it refers to an element generally refers to the right end of the element, as shown in the figures. The vaso-occlusive assembly 10 generally comprises a delivery device 12, which includes an elongated tubular catheter 16 and a pusher member 18, and a vaso-occlusive device 14 detachably associated with the distal end of the delivery device 12, and in particular, the distal end of the pusher member 18.

The catheter 16 comprises an elongated tubular member 20 having a delivery lumen 22 in which the pusher member 18, and thus, the vaso-occlusive device 14, is slidably disposed. The tubular member 20 can be composed of any suitable flexible and biocompatible material that allows it to be introduced through the tortuous vasculature of a patient to the vascular occlusion site. The pusher member 18 has a severable junction 24 that operates to selectively detach the vaso-occlusive device 14 from the delivery device 12. In the illustrated embodiment, the severable junction 24 is an electrolytically severable junction that is susceptible to electrolysis, and thus, disintegrates when the core wire 18 is electrically charged in the presence of an ionic solution, such as blood or most other bodily fluids.

To provide the electrical charge, the catheter 16 further comprises an annular electrode 26 mounted on the tubular member 20 at the distal end of the delivery lumen 22 and electrical conductors 28 (two shown) axially extending through the wall of the tubular member 20 in contact with the electrode 26. The electrode 26 comprises a conductive biocompatible material, such as stainless steel, titanium, copper, platinum, gold, silver, or alloys thereof. Thus, when the electrolytically severable junction 24 is disposed outside of the catheter 16 in contact with the bodily fluids of the patient, electrical energy can be transmitted through the conductors 28 to the electrode 26, where it is transmitted to the portion of the core wire 18 in contact with the electrode 26. The electrical energy is then transmitted through the core wire 18 to the electrolytically severable junction 24, which undergoes electrolysis until it severs to detach the vaso-occlusive device 14 from the delivery device 12. Further details regarding the use of electrolytic joints are described in U.S. Pat. Nos. 5,354,295, 5,122,136, and 5,941,888, which are expressly incorporated herein by reference.

It should be noted that other types of severable junctions, such as mechanically severable junctions, can also be used to connect the vaso-occlusive device 14 to the pusher member 18. Various mechanical mechanisms are described in U.S. Pat. Nos. 5,234,437, 5,250,071, 5,261,916, 5,304,195, 5,312,415, and 5,350,397, which are expressly incorporated herein by reference.

Referring still to FIG. 1, the vaso-occlusive device 14 includes a vaso-occlusive member 30 having a lumen 32 extending therethrough, a stretch-resisting member 34 extending within the lumen 32 of the vaso-occlusive member 30 to prevent axial stretching of the vaso-occlusive member 30, and a pivotable coupling 36 that operates to affix the vaso-occlusive member 30 to the core wire 18, while providing a pivot point 38 about which the distal end of the pusher member 18 and the vaso-occlusive member 30 pivot in order to deflect an axial force otherwise applied to the delivery device 12 by the vaso-occlusive device 14 after the junction 24 has been severed. In the illustrated embodiment, the pivotable coupling 36 also serves as an anchoring assembly that facilitates anchoring of the stretch-resisting member 34 within the vaso-occlusive member 30.

The vaso-occlusive member 30 has a sufficient small size that enables it to be advanced through the delivery catheter 16 and access the targeted vascular site. The materials used in constructing the vaso-occlusive member 30 may be any of a wide variety of materials, and preferably, a radio-opaque and biologically compatible material. Suitable metallic materials include the Platinum Group metals, especially platinum, rhodium, palladium, rhenium, as well as tungsten, gold, silver, tantalum, and alloys of these metals. Highly preferred is a platinum/tungsten alloy, e.g., 8% tungsten and the remainder platinum. Certain polymers can also be used as a suitable material for the vaso-occlusive member 30 either alone or in conjunction with radio-opaque markers, e.g., by filling the polymer with radio-opaque material, such as powdered tantalum, powdered tungsten, bismuth oxide, barium sulfate, and the like.

In the illustrated embodiment, the primary vaso-occlusive member 30 takes the form of a helical coil with windings 40, although other suitable members, such as a ribbon, a braided member, or the like can be used. The shape and constituent of the vaso-occlusive coil 30 will depend upon the use to which the coil will be placed. For occluding peripheral or neural sites, the diameter of the wire used in the production of the coil 30 is preferably in the range of 0.001 to 0.006 inches, and the outer diameter of the vaso-occlusive coil 30, itself, is preferably in the range of 0.003 and 0.025 inches. For most neurovascular applications, an outer diameter between 0.008 and 0.018 inches provides sufficient hoop strength to hold the vaso-occlusive coil 30 in place within the selected body site, without substantially distending the wall of the site and without moving from that site as a result of the repetitive fluid pulsing found in the vascular system. The axial length of the wire used to make the vaso-occlusive coil 30 will usually fall in the range of 0.5 and 100 cm, more typically within the range of 2.0 and 40 cm. The axial length of the vaso-occlusive coil 30 will usually fall within the range of 2 mm and 40 cm. It should be noted that all of the dimensions provided for the vaso-occlusive coil 30 are provided only as guidelines, and the invention, in its broadest aspects, should not be limited thereto. Rather, only dimensions that are suitable for use in occluding sites within the human body are included in the scope of the invention. It should be appreciated that while the length of the vaso-occlusive coil 30 is shown in FIG. 1 as being on the same order of length as the pivotable coupling 26, the length of the vaso-occlusive coil 30 will typically be many orders greater than that of the pivotable coupling 26.

Depending on the desired therapeutic effect and the shape of the site to be treated, the vaso-occlusive coil 30 may be treated or accessorized in numerous ways in order to enhance its therapeutic effect. For example, the vaso-occlusive coil 30 may be made to form various secondary shapes, often through the use of heat treatment, that may be better suited to fill a particular treatment site, as disclosed in U.S. Pat. Nos. 5,853,418 and 6,280,457, which are expressly incorporated herein by reference. Alternatively, the vaso-occlusive coil 30 may have little or no shape after introduction into the vascular space, as disclosed in U.S. Pat. No. 5,690,666, which is expressly incorporated herein by reference. In addition, external materials may be added to the outside of vaso-occlusive coil 30 in an effort to increase its thrombolytic properties. For example, fibrous materials can be tied or braided onto the outside of the vaso-occlusive coil 30. These alternative embodiments are disclosed in U.S. Pat. Nos. 5,226,911, 5,304,194, 5,354,295, 5,382,259, 5,549,624, and 6,280,457, which are expressly incorporated herein by reference.

Referring still to FIG. 1, the stretch-resisting member 34 is affixed between the distal end of the vaso-occlusive coil 30 and the distal end of the pivotable coupling 36 within the lumen 22 of the vaso-occlusive coil 30 in a tensile relationship to prevent axial stretching of the vaso-occlusive coil 30. In the illustrated embodiment, the stretch-resisting member 34 comprises a distal cap 42 affixed outside of the distal end of the vaso-occlusive coil 30, and a looped thread 44 coupled to the pivotable coupling 36 in a tensile relationship, such that the distal cap 42 is proximally urged against the distal end of the vaso-occlusive coil 30. The distal cap 42, which has a diameter greater than the diameter of the coil lumen 22, can be formed by gluing or melting the distal end of the stretch-resisting member 34. Alternatively, the stretch-resisting member 34 may be tied in a knot (not shown), which may or may not be attached to the vaso-occlusive coil 30.

In the illustrated embodiment, the stretch-resisting member 34 is fibrous and desirably polymeric. Suitable polymeric materials can be either thermosetting or thermoplastic and can comprise a bundle of threads or a single filament. Thermoplastics are preferred, because they allow simplification of the procedure for constructing the stretch-resisting member, e.g., by allowing the distal cap 42 to be formed by melting using a simple tool, such as a soldering iron. Suitable polymers include most biocompatible materials that may be made in fibers, including thermoplastics, e.g., polyesters, such as polyethyleneterephthalate (PET), especially Dacron®; polyamides, including Nylon®; polyolefins, such as polyethylene, polyprophylene, polybutylene, their mixtures, alloys, block, and random copolymers; fluoropolymers (polytetrafluoroethylene (PTFE)), or even silk or collagen. The stretch-resisting member 34 may be composed from materials, such as dissolvable sutures, for instance, polylactic acid or polyglycolic acid, to encourage cell growth in an aneurysm after introduction. Highly preferred is polypropylene, for instance, in the form of 10-0 and 9-0 polypropylene suture material. The diameter of the looped thread 44 is typically between about 0.0001 inches and 0.01 inches.

Alternatively, rather than using plastics, a wide variety of stainless steels can be used if some sacrifice in flexibility can be tolerated. Stretch-resisting members of this type are described in U.S. Pat. No. 5,853,418, which is expressly incorporated herein by reference. Very desirable materials of construction, from a mechanical point of view, are materials that maintain their shape despite being subject to high stress. Certain "super-elastic alloys" include various nickel-titanium alloys (48-58 atomic % nickel and optionally containing modest amounts of iron); copper/zinc alloys containing 1-10 weight % of beryllium, silicon, tin, aluminum, or gallium; or nickel/aluminum alloys (36-38 atomic % aluminum).

The pivotable coupling 36 comprises a proximal mounting coil 46 formed of a series of windings 50, a distal mounting coil 48 formed of a series of windings 52, and a flexible sleeve 54 for coupling the mounting coils 46, 48 together. The proximal mounting coil 46 is mounted around the distal end of the core wire 18 just distal to the severable junction 24, and the distal mounting coil 48 is mounted within the lumen 22 of the vaso-occlusive coil 30. The distal-most winding 52 of the distal mounting coil 48 is formed into a loop or hook 56, which is suitably connected to the looped thread 44 of the stretch-resisting member 34, thereby maintaining the stretch-resisting member 34 in a tensile state.

The mounting coils 46, 48 can be composed of the same material as the vaso-occlusive coil 30, but in the illustrated embodiment, are composed of platinum or platinum alloy. In the illustrated embodiment, the diameter of the wire used to make the mounting coils 46, 48 is smaller than the diameters of the wire used to make the vaso-occlusive coil 30 in order to minimize the profile of the pivotable coupling 36. The outer diameter of the distal mounting coil 48 is preferably about the same size as the diameter of the primary coil lumen 22, so that the distal mounting coil 48 and vaso-occlusive coil 30 snugly fit together.

The pivotable coupling 36 further comprises a core wire extension 58 around which the distal mounting coil 48 is mounted to provide the distal end of the pivotable coupling 36 the compressive strength necessary to prevent buckling when mounted within the lumen 22 of the vaso-occlusive coil 30. The mounting coils 46, 48 can be affixed to the core wire 18, core wire extension 58, and vaso-occlusive coil 30 using suitable means, such as interference fitting, welding, or bonding.

The sleeve 54 is suitably mounted around the mounting coils 46, 48, and is composed of a highly flexible, yet axially strong material, such that it is configured to axially connect the mounting coils 46, 48, while allowing the mounting coils 46, 48 to pivot relative to each other about the pivot point 38, as illustrated in FIG. 2. Suitable materials for the sleeve 54 include elastomeric polymers, which can be heat shrunk or otherwise bonded over the mounting coils 46, 48. Fibrous material may also be embedded within the sleeve 54 to increase its axial strength. The pivot point 38 can either be coincident within a space between the ends of the mounting coils 46, 48 or a highly flexible material, such as an elastomeric polymer, that can be bonded between the mounting coils 46, 48. As previously discussed, the outer diameters of the respective mounting coils 46, 48 are preferably the same, so that the sleeve 54 fits over the mounting coils 46, 48 in a uniformly snug manner.

Besides integrating the mounting coils 46, 48 in an axially fixed, but pivotably, relationship, the sleeve 54 also serves to electrically insulate the mounting coils 46, 48, as well as the distal end of the core wire 18 and the core wire extension 58, from the bodily fluids in which they would otherwise be in contact with, so that the electrolytic process is focused at the severable junction 24. In addition, the proximal-most windings 40 of the vaso-occlusive coil 30 in which the distal mounting coil 48 is affixed can be coated with an electrically insulative material, such as polyurethane or the like, to prevent potential electrical contact between the vaso-occlusive coil 30 and the core wire 18.

Optional electrically conductive coils (not shown) can be mounted to the coil wire 18 between the pivotable coupling 36 and the severable junction 24 to provide a means to determine when the vaso-occlusive device 14 has detached from the core wire 18. That is, the electrically conductive coils provide an increased conductance between the core wire 18 and an external electrode, the substantial reduction of which can be measured when the conductive coils are eliminated from the electrical circuit after the conductive coils (along with the vaso-occlusive device 14) separates from the core wire 18.

Referring now to FIG. 3, a vaso-occlusive assembly 110 constructed in accordance with another preferred embodiment is illustrated. The vaso-occlusive assembly 110 is similar to the previously described vaso-occlusive assembly 10, with the exception that it comprises a vaso-occlusive device 114 that includes a different pivotable coupling 36 for affixing the vaso-occlusive coil 30 to the core wire 18. Like the previously described pivotable coupling 36, the pivotable coupling 136 illustrated in FIG. 3 has a proximal mounting coil 146 with windings 150 affixed to the distal end of the core wire 18 and a distal mounting coil 148 with windings 152 affixed within the lumen 22 of the vaso-occlusive coil 30. These mounting coils 146, 148, however, are not connected together via a sleeve-based pivotable coupling, but rather a link-based pivotable coupling 136.

Figure 4:
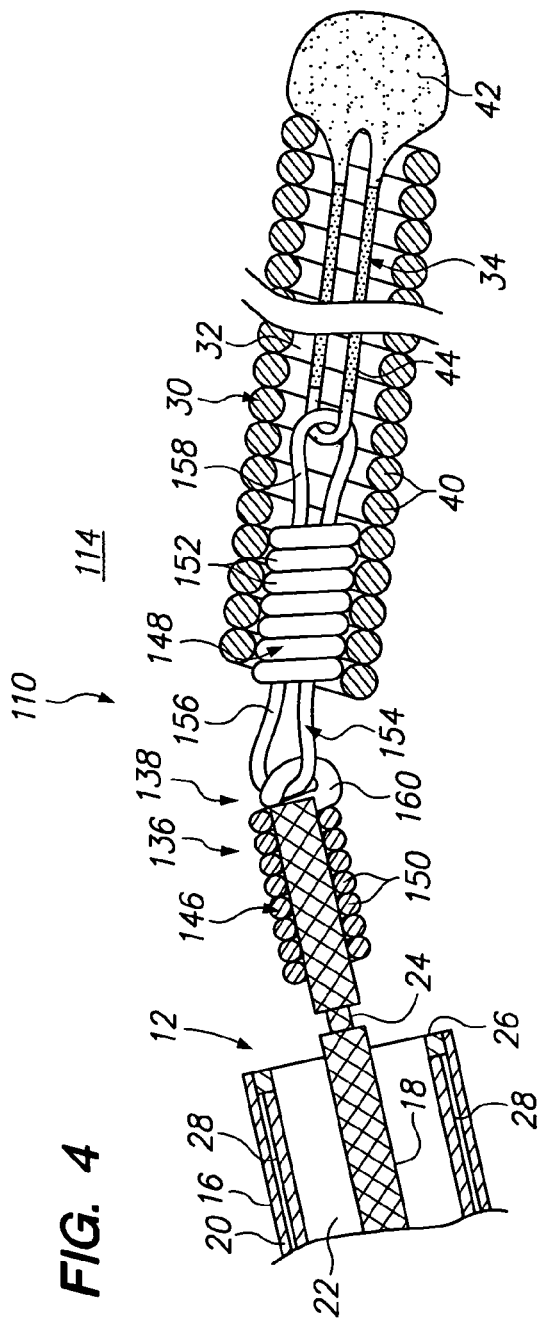
FIG. 4 is a cross-sectional view of the vaso-occlusive assembly of FIG. 3, particularly illustrating operation of a pivotable coupling within the assembly.

In particular, the pivotable coupling 136 comprises a loop member 154 disposed through the lumen of the distal mounting coil 148, so that proximal and distal eyelets 156, 158 respectively extend from the opposite sides of the distal mounting coil 148. The loop member 154 may be suitably affixed within the lumen of the distal mounting coil 148 using an interference fit or by bonding or welding. The pivotable coupling 136 also comprises a hook 160 formed from the distal-most winding 150 of the proximal mounting coil 146. The hook 160 is linked around the proximal eyelet 156 of the loop member 154 to axially connect the mounting coils 146, 148 to each other, while allowing the mounting coils 146, 148 to pivot relative to each other about a pivot point 138, as illustrated in FIG. 4. Significantly, the hook 160 and proximal eyelet 156 are not welded or bonded together, so as to not hinder the pivoting action of the coupling 136.

Like the previously described pivotable coupling 36, the pivotable coupling 136 in this case also serves as an anchoring assembly for anchoring the stretch-resisting member 34 within the vaso-occlusive coil 30. In particular, the distal eyelet 158 of the looped member 154 connects to the looped thread 44 of the stretch-resisting member 34 to maintain the stretch-resisting member 34 in a tensile state. The mounting coil 146, the proximal loop 156 of the looped member 154, and the proximal-most windings 40 of the vaso-occlusive coil 30 can be coated with an electrically insulative material (not shown), such as polyurethane or the like, to prevent potential electrical contact between the vaso-occlusive coil 30 and the core wire 18. Optionally, the mounting coil 146 can be left bare to provide a means to determine when the vaso-occlusive device 114 has detached from the core wire 18.

Figure 5:
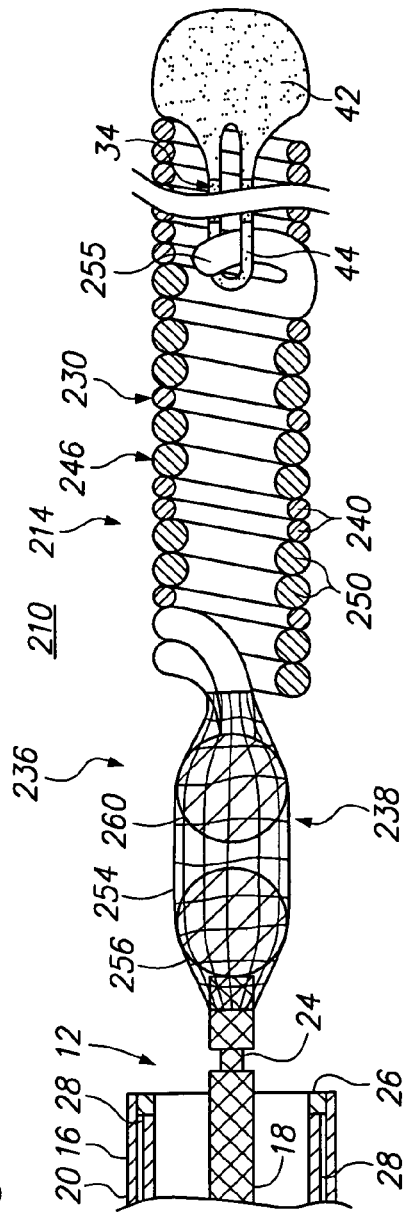
FIG. 5 is a cross-sectional view of a vaso-occlusive assembly constructed in accordance with still another preferred embodiment of the present inventions.

Referring now to FIG. 5, a vaso-occlusive assembly 210 constructed in accordance with still another preferred embodiment is illustrated. The vaso-occlusive assembly 210 is similar to the previously described vaso-occlusive assemblies 10, 110, with the exception that it comprises a vaso-occlusive device 214 with a different pivotable coupling 236 for affixing a modified vaso-occlusive coil 230 to the core wire 18. In particular, the pivotable coupling 236 comprises a mounting coil 246 having windings 250 affixed to proximal-most windings 240 of the vaso-occlusive coil 230 (mounting coil 246 and vaso-occlusive coil 230 shown separately in FIG. 7), a pair of ball elements 256, 260 disposed on the respective distal end of the core wire 18 and proximal-most winding 250 of the mounting coil 246, and a flexible sleeve 254 for coupling the ball elements 256, 260 together.

Figure 7:
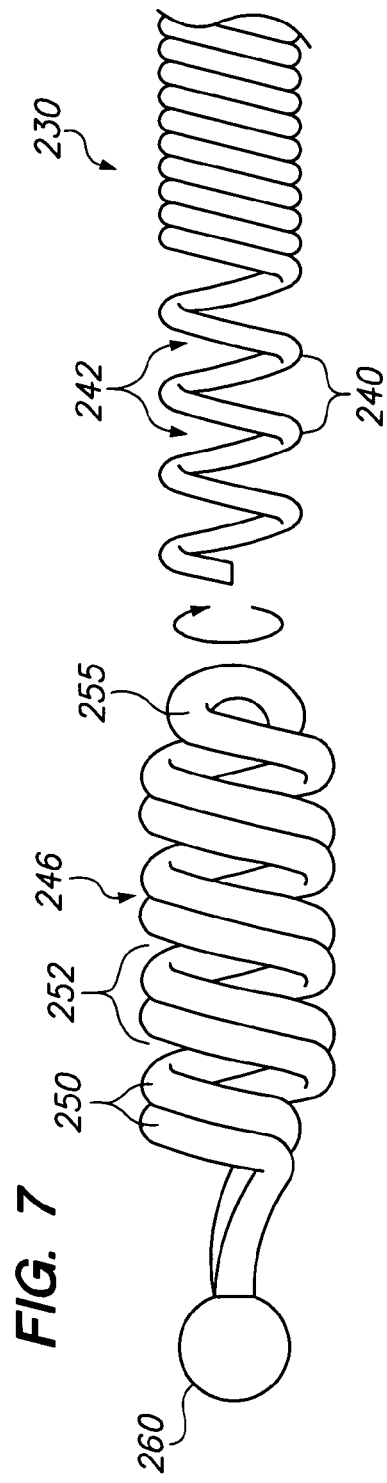
FIG. 7 is an exploded view of a pivotable coupling and vaso-occlusive coil used in the vaso-occlusive assembly of FIG. 5.

The mounting coil 246 and vaso-occlusive coil 230 are designed to be affixed to each other in an interlocking manner. In particular, the windings 246 of the mounting coil 230 and the proximal-most windings 240 of the vaso-occlusive coil 230 are open-pitched (best shown in FIG. 7), so that the mounting coil windings 246 can be disposed within spaces 242 between the open vaso-occlusive coil windings 240, and the vaso-occlusive coil windings 230 can likewise be disposed within spaces 252 between the open mounting coil windings 250. It can be appreciated, that the mounting coil 246 and vaso-occlusive coil 230 can be interlocked together using a twisting action, as illustrated in FIG. 7. To ensure that the mounting coil 246 and vaso-occlusive coil 230 remain interlocked, they may be suitably welded or bonded together. The composition and dimensions of the vaso-occlusive coil 230 may be similar to those of the previously described vaso-occlusive coil 30.

The mounting coil 246 preferably has a sufficient strength and stiffness that allows it to be integrated with the vaso-occlusive coil 230 in a robust manner. To this end, the windings 250 of the mounting coil 246 are doubled up, so that the spaces 252 only exist between pairs of windings 250. That is, there are twice as many windings 250 as spaces 252, thereby effectively increasing the strength of the mounting coil 246 relative to the vaso-occlusive coil 230. To provide additional strength, the wire used to make the mounting coil 246 has an increased diameter relative to the diameter of the wire used to make the vaso-occlusive coil 230.

The outer diameters of the respective vaso-occlusive coil 230 and mounting coil 246 are selected to be the same, so that the outer profile of the combined assembly is uniform. The dimensions of the spaces 242 between the open windings 240 of the vaso-occlusive coil 230 will depend on the size and number of windings 250 of the mounting coil 246, and the dimensions of the spaces 252 between the windings 250 of the mounting coil 246 will likewise depend on the size and number of windings 240 of the vaso-occlusive coil 230. In the illustrated embodiment, the width of the spaces 242, 252 of one coil 230, 246 will be selected to conveniently accommodate the windings 250, 240 of the other coil 246, 230, so that a substantial axial force is not exerted on the respective windings of the coils 230, 246. Thus, the width of the spaces 242 between the windings 240 of the vaso-occlusive coil 230 will be about equal to twice the diameter of the wire used to make the mounting coil 246, whereas the width of the spaces 252 between the windings 250 of the mounting coil 246 will be about equal to the diameter of the wire used to make the vaso-occlusive coil 230.

Figure 6:
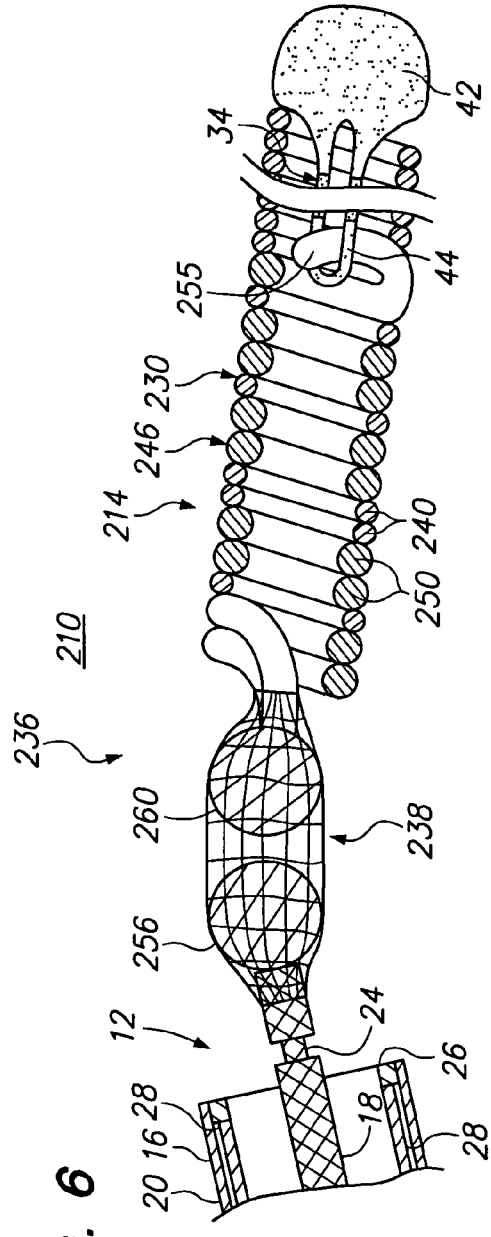
FIG. 6 is a cross-sectional view of the vaso-occlusive assembly of FIG. 5, particularly illustrating operation of a pivotable coupling within the assembly.

The ball members 256, 260 may be formed, e.g., by melting the ends of the respective core wire 18 and mounting coil 246. The sleeve 254 is suitably mounted around the ball members 254, 260, and is composed of a highly flexible, yet axially strong material, such that it is configured to axially connect the ball members 254, 260 while allowing the ball members 254, 260 to pivot relative to each other about a pivot point 238, as illustrated in FIG. 6.

The pivotable coupling 236, like the pivotable couplings 36, 136 described above, additionally serves as an anchoring assembly that anchors the stretch-resisting member 34 within the vaso-occlusive coil 230. To this end, the doubling of the mounting coil windings 250 naturally forms an eyelet 255 (best shown in FIG. 7) at the distal end of the mounting coil 246 that is suitably connected to the looped thread 44 of the stretch-resisting member 34, thereby maintaining the stretch-resisting member 34 in a tensile state.

In the illustrated embodiment, the sleeve 254 comprises a mesh material to provide the sleeve 254 with maximum flexibility. Because, the mesh sleeve 254 does not electrically isolate the ball members 256, 260, the ball members 256, 260 can be coated with an electrically insulative material (not shown), such as polyurethane or the like, to prevent potential electrical contact between the vaso-occlusive coil 230 and the core wire 18. Optionally, the proximal ball member 256 can be left bare to provide a means to determine when the vaso-occlusive device 214 has detached from the core wire 18.

Referring now to FIG. 8, a vaso-occlusive assembly 310 constructed in accordance with yet another preferred embodiment is illustrated. The vaso-occlusive assembly 310 is similar to the previously described vaso-occlusive assemblies 10, 110, 210, with the exception that it comprises a vaso-occlusive device 314 with a different pivotable coupling 336 for affixing a modified vaso-occlusive coil 330 to the core wire 18. In particular, the pivotable coupling 336 comprises a proximal mounting coil 346 with windings 350 affixed to the distal end of the core wire 18, and a distal mounting coil 338 within windings 352 affixed to the windings 350 of the proximal mounting coil 346 and windings 340 of the vaso-occlusive coil 330 (mounting coils 346, 348 and vaso-occlusive coil 330 shown separately in FIG. 10).

Like the previously described mounting coil 246 and vaso-occlusive coil 230, the mounting coils 346, 348 and vaso-occlusive coil 330 are designed to be affixed to each other in an interlocking manner. In particular, the distal-most windings 350 of the proximal mounting coil 346, all of the windings 350 of the distal mounting coil 346, and the proximal-most windings 340 of the vaso-occlusive coil 330 are open-pitched (best shown in FIG. 10). In this manner, the distal-most coil windings 350 of the proximal mounting coil 346 can be disposed within spaces 356 between the proximal-most windings 352 of the distal mounting coil 348, and the proximal-most windings 352 of the distal mounting coil 348 can likewise be disposed within spaces 354 between the distal-most coil windings 350 of the proximal mounting coil 346. In a similar manner, the proximal-most windings 340 of the vaso-occlusive coil 330 can be disposed within the spaces 356 between the distal-most windings 352 of the distal mounting coil 348, and the distal-most windings 352 of the distal mounting coil 348 can likewise be disposed within spaces 342 between the proximal-most windings 340 of the vaso-occlusive coil 330.

Figure 10:
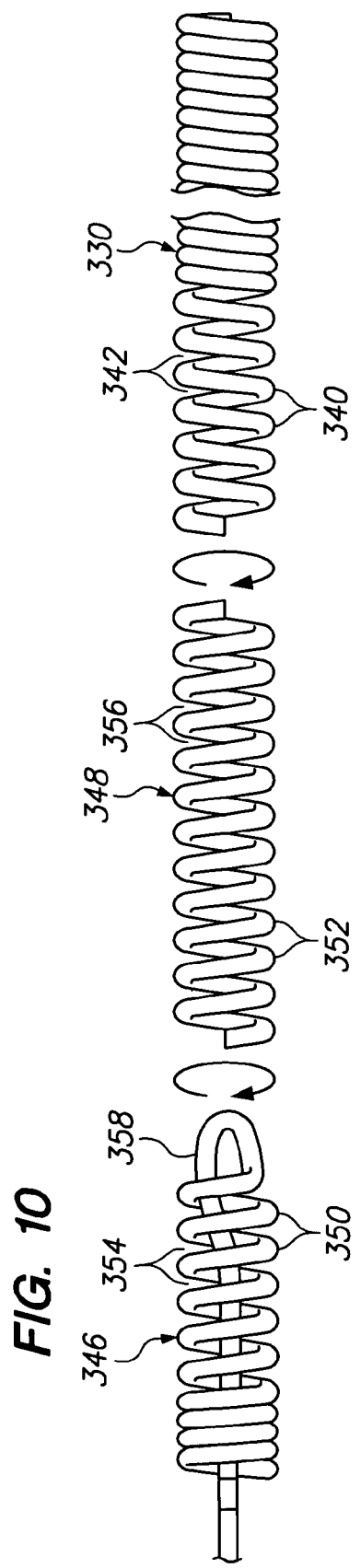
FIG. 10 is an exploded view of a pivotable coupling and vaso-occlusive coil used in the vaso-occlusive assembly of FIG. 8, and FIGS. 11A-11C illustrate a method of using the vaso-occlusive assembly of FIG. 1 to occlude an aneurysm.

It can be appreciated, that the distal and proximal mounting coils 346, 348 and vaso-occlusive coil 330 can be interlocked together using a twisting action, as illustrated in FIG. 10. To ensure that the distal and proximal mounting coils 346, 348 and vaso-occlusive coil 330 remain interlocked, they may be suitably welded or bonded together. The composition and dimensions of the vaso-occlusive coil 330 may be similar to those of the previously described vaso-occlusive coil 30.

The outer diameters of the distal and proximal mounting coils 346, 348 and vaso-occlusive coil 330 are selected to be the same, so that the outer profile of the combined assembly is uniform. In the same manner described above with respect to the mounting coil 246 and vaso-occlusive coil 230, the dimensions of the spaces between the open windings of each coil will depend on the size and number of the windings of the coil that interlocks with the respective coil.

The number of windings of the distal mounting coil 348 is greater than the combined number of windings of the proximal mounting coil 346 and vaso-occlusive coil 330, so that the spaces between the windings at the center of the distal mounting coil 346 remain empty. In this manner, a pivot point 338 about which the proximal and distal portions of the distal mounting coil 348 may pivot, is formed in the center of the distal mounting coil 348.

The pivotable coupling 336, like the pivotable couplings 36, 136, 236 described above, additionally serves as an anchoring assembly that anchors the stretch-resisting member 34 within the vaso-occlusive coil 330. To this end, the proximal mounting coil 346 is formed by coiling the distal end of the core wire 18 onto itself, as illustrated in FIG. 10. An eyelet 358 is formed at the distal end of the proximal mounting coil 348 where the core wire 18 coils back is suitably connected to the looped thread 44 of the stretch-resisting member 34, thereby maintaining the stretch-resisting member 34 in a tensile state.

The proximal and distal mounting coils 346, 348 and the proximal-most windings 340 of the vaso-occlusive coil 330 can be coated with an electrically insulative material (not shown), such as polyurethane or the like, to prevent potential electrical contact between the vaso-occlusive coil 330 and the core wire 18. The distal portion of the core wire 18 extending through the proximal mounting coil 346 may also be coated with an electrically insulative material. Optionally, this portion of the core wire 18 can be left bare to provide a means to determine when the vaso-occlusive device 314 has detached from the core wire 18.

Although the pivotable couplings of the previous vaso-occlusive assemblies have been described as being located distal to the severable junction, pivotable couplings can also be located proximal to the severable junction.

Having described the structure of the vaso-occlusive assemblies, the operation of the vaso-occlusive assembly 100 in occluding a vascular site, and in particular, an aneurysm 400 originating from a parent blood vessel 402, will now be described with reference to FIGS. 11A-11C. The vaso-occlusive assemblies 110, 210, 310 can similarly be used to occlude the aneurysm 400, but for purposes of brevity, only the use of the vaso-occlusive assembly 10 will be described.

Figure 11A:
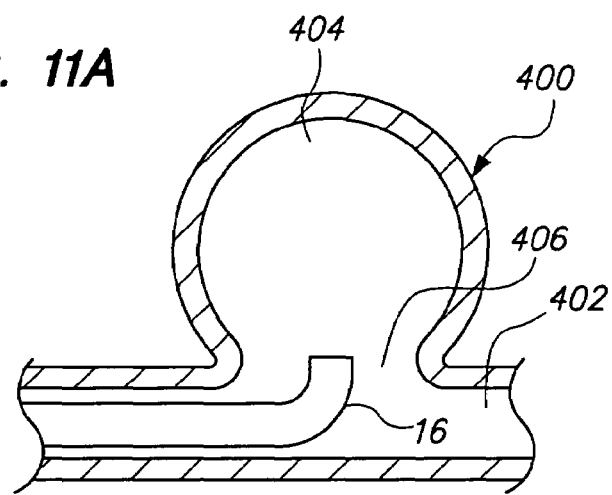
Figure 11B:
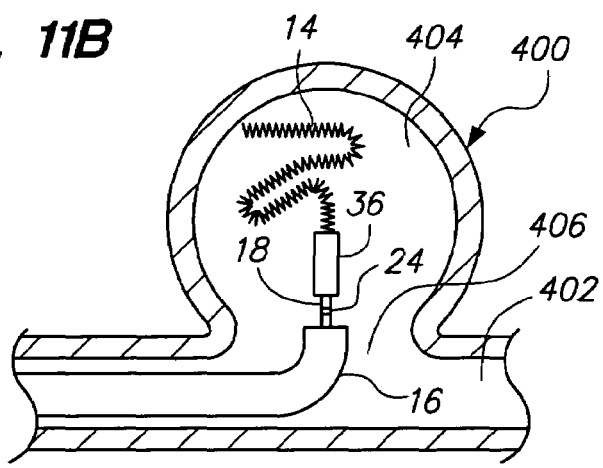
Figure 11C:
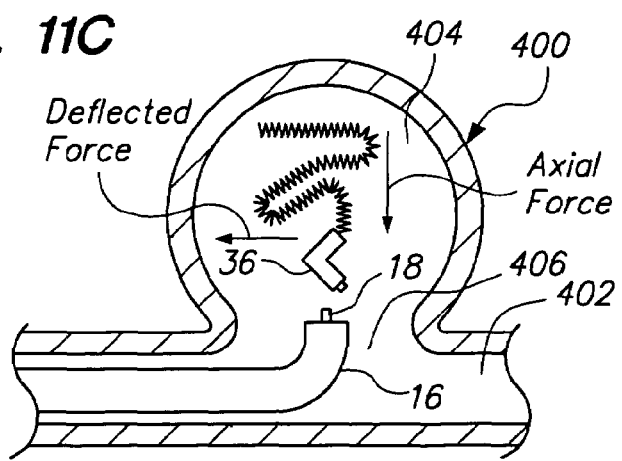

First, in a conventional manner, the catheter 16, which houses the core wire 18 and vaso-occlusive coil 14, is introduced through the vasculature of the patient and manipulated until the distal end of the catheter 16 resides within a neck 402 of the aneurysm 400 (FIG. 11A). At this point, the vaso-occlusive coil 14 is positioned at the distal end of the catheter 16 in its undeployed state. The core wire 18 is then pushed in the distal direction, causing the vaso-occlusive coil 14 to extend out of the distal end of the catheter 16 and deploy within a sac of the 404 of the aneurysm 400 (FIG. 11B). A current is then applied to the core wire 18 (via the electrode 26 illustrated in FIG. 1), which causes the severable junction 24 to disintegrate via electrolysis, after which the vaso-occlusive coil 14 detaches from the core wire 18 (FIG. 11C). During detachment, the vaso-occlusive coil 14 creates an axial force in the proximal direction that causes the flexible coupling 36 to buckle, thereby deflecting the axial force in the lateral direction, so that the catheter 16 is not displaced from the aneurysmal neck 404 by the axial force.

Additional vaso-occlusive coils 14 can be deployed within the aneurysmal sac 402 in a similar manner to completely occlude the aneurysm 400. After occlusion of the aneurysm 400 is completed, the vaso-occlusion assembly 10 is removed from the vasculature of the patient.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. An assembly for occluding a vascular site of a human or veterinary patient, the assembly comprising:
    a vaso-occlusive coil;
    a pusher member comprising an elongate core wire having a distal end and a junction comprising a severable segment susceptible to electrolysis located proximal to the distal end of the elongate core wire;
    a coupling comprising a proximal mounting coil mounted on the distal end of the elongate core wire and a distal mounting coil mounted to the vaso-occlusive coil; and
    a flexible sleeve comprising an elastomeric polymer fixedly secured to a periphery of the proximal mounting coil and the distal mounting coil, the flexible sleeve being configured such that the proximal mounting coil and the distal mounting coil pivot relative to each other about a pivot point, and wherein the proximal mounting coil and the distal mounting coil are contained in the flexible sleeve in a spaced apart configuration and remain in the spaced apart configuration within the flexible sleeve after the severable segment has been severed.

2. The assembly of claim 1, wherein the coupling electrically insulates the core wire distal end from the vaso-occlusive coil.

3. The assembly of claim 1, further comprising a catheter having a delivery lumen in which the elongate core wire is slidably disposed.

4. The assembly of claim 1, wherein a distal-most winding of the distal mounting coil is configured in the shape of a loop or hook.

5. The assembly of claim 1, further comprising a stretch-resistant member affixed between a distal end of the vaso-occlusive coil and a distal end of the coupling, wherein the stretch-resistant member comprises a distal cap affixed to an outside surface of the distal end of the vaso-occlusive coil.

* * * * *